United States Patent
García Echevarrieta et al.

(10) Patent No.: US 12,185,815 B2
(45) Date of Patent: Jan. 7, 2025

(54) DEVICE FOR TESTING FRAGRANCES AND THE LIKE

(71) Applicant: ANTONIO PUIG, S.A., L'Hospitalet de Llobregat (ES)

(72) Inventors: Alejandro García Echevarrieta, Barcelona (ES); David Panyella Costa, Barcelona (ES); Jordi Vidal Tasa, Barcelona (ES)

(73) Assignee: ANTONIO PUIG, S.A., L'Hospitalet de Llobregat (ES)

( * ) Notice: Subject to any disclaimer, the term of this patent is extended or adjusted under 35 U.S.C. 154(b) by 104 days.

(21) Appl. No.: 17/611,050

(22) PCT Filed: May 24, 2019

(86) PCT No.: PCT/ES2019/070349
§ 371 (c)(1),
(2) Date: Nov. 12, 2021

(87) PCT Pub. No.: WO2020/240051
PCT Pub. Date: Dec. 3, 2020

(65) Prior Publication Data
US 2022/0167723 A1 Jun. 2, 2022

(51) Int. Cl.
*A45D 34/02* (2006.01)
*A45D 34/00* (2006.01)
*A61L 9/12* (2006.01)

(52) U.S. Cl.
CPC ............ *A45D 34/02* (2013.01); *A61L 9/12* (2013.01); *A45D 2034/007* (2013.01); *A45D 2200/051* (2013.01); *A61L 2209/13* (2013.01)

(58) Field of Classification Search
CPC ............ A45D 34/02; A45D 2034/007; A45D 2200/051; A61L 9/12; A61L 2209/13
(Continued)

(56) References Cited

U.S. PATENT DOCUMENTS 4,621,768 A 11/1986 Lhoste et al.
4,915,301 A * 4/1990 Munteanu ............... A61L 9/01
239/45

(Continued)

FOREIGN PATENT DOCUMENTS

EP 0167657 A2 1/1986
EP 0178228 A1 4/1986
(Continued)

OTHER PUBLICATIONS

International Search Report and Written Opinion mailed Feb. 6, 2020 for Application No. PCT/ES2019/070349, 14 pages.

*Primary Examiner* — Christopher S Kim
(74) *Attorney, Agent, or Firm* — Squire Patton Boggs (US) LLP

(57) ABSTRACT

The device (100) comprises a container (200) for containing a fragrance (300) having at least one opening (450), an absorbing element (500) with a first portion (510) to be received within the container (200) continuously in direct contact with the fragrance (300) and with a second portion (520) at least partially outside the container (200) arranged through the opening (450), and a cover (600) that can be made at least partially of an absorbing material, which covers, in at least a substantially fluid-tight and impermeable manner, and at least partially, the second portion (520) of the absorbing element (500).

16 Claims, 2 Drawing Sheets

(58) Field of Classification Search
USPC .................................................. 239/44, 45
See application file for complete search history.

(56) References Cited

U.S. PATENT DOCUMENTS 7,007,863 B2    3/2006   Kotary et al.
8,844,837 B1 *  9/2014   Pesu ..................... A61L 9/127
                                                     239/289

FOREIGN PATENT DOCUMENTS

EP            0872193 A1    10/1998
FR            2905870 A1     3/2008
WO    WO 2012/123664 A1     9/2012

* cited by examiner

DEVICE FOR TESTING FRAGRANCES AND THE LIKE

CROSS-REFERENCE

The present application is a 35 USC 371 national phase filing of PCT/ES2019/070349 filed on May 24, 2019, which is incorporated herein by reference in entirety.

The present disclosure relates to a device for testing fragrances and the like, in particular, perfumes. The present device is however also applicable to a wide range of other fragrances, such as, for example, detergents, oils, softeners, air fresheners, etc. The device is applicable, in general, to liquid or gel-like odour compositions that can be tested before being acquired.

BACKGROUND

Applying a fragrance, for example, by spraying, to a strip of paper and then smelling it in order to test the fragrance is known. The strip of paper allows the fragrance to be dispensed so that it can be either acquired or discarded by the user.

Paper strips or blotters have the advantage of being simple and cost-effective means to test a fragrance. In addition, paper strips provide fresh odour by facilitating evaporation of ethanol usually contained, for example, in perfumes. However, paper strips have the disadvantage that fragrance odour evolves over time, resulting in different odour profiles, with which the user may come to perceive a different odour than that of the fragrance that is actually going to acquire. Another disadvantage of the paper strips is that waste is generated as they are discarded after use.

One alternative to overcome these disadvantages of the paper strips has been to replace them with ceramic bodies, which may take different shapes, and made of ceramic material, such as, for example, by pressing and firing. As with the paper strips, a fragrance is applied to the ceramic bodies, for example, by spraying, for subsequently smelling. A further disadvantage associated with the use of conventional paper strips relates to environment olfactory contamination due to the fact of having to perfume by spraying or immersion at the same test point, which negatively influences perception of odour to be tested.

EP2211660 discloses a device of the above type for presenting a fragrance. The device includes a presentation stick comprising a confining enclosure for containing a fragrance and a porous element made of, for example, a ceramic material. The porous element is arranged to plug a neck in the confining enclosure to be received therein, in a zone in which the fragrance exists only in the gaseous state. The presentation stick has a holding head to plug the neck of the confining enclosure. To test the fragrance, the user removes the presentation stick from the confining enclosure which, as it is impregnated with the fragrance vapor, it is delivered it to the outside.

In the device of EP2211660, the fragrance is applied to the porous element so that it is loaded and stored closed within the enclosure so that it does not evaporate quickly. The fragrance, once applied, evolves within the enclosure, even if it is closed. With each use, this fragrance retained by the porous element evaporates. Fragrance time is thus heavily dependent on the number of consecutive uses. If, for example, with the same perfume protocol in a day, few fragrance applications are performed, and the next day many other fragrance applications are performed, the next day's client perception does not have much to do with the previous day's client perception.

In EP3177172 a device for testing a perfume is provided. This device comprises a housing having an opening, and a test body which can be impregnated with perfume and which is capable of being at least partially inserted into the housing through the opening. A perfume-dispensing device is arranged within the housing for dispensing perfume when the test body is inserted into the housing. The perfume-dispensing device comprises at least one perfume-impregnating body with which the test body contacts when inserted into the housing, impregnating the test body with perfume.

In the device of EP3177172, the test body is inserted into the perfumed composition at the time of testing, so as to be impregnated and smelled. The ceramic of the test body is impregnated with the formulation without leaving time for the ceramic to collect the amount that it is capable of retaining. There remains, therefore, unabsorbed perfume residues that will be over-represented by the more volatile notes such as ethanol, so that olfactory experience is not faithful to the perfume and is not complete either. On the other hand, since the test body is impregnated and dried in each use, the oxidation process of the perfume residues remaining in the ceramic is very important, causing bad odours by oxidation.

In addition to the aforementioned disadvantages and, in spite of the fact that these solutions of the prior art overcome some of the disadvantages related to paper strips, since, for example, no waste is generated as they are not frequently discarded, the use of a ceramic body with the configuration described in said documents is not without many other drawbacks. First, ceramic bodies provide a very intense smell in alcohol and do not have time to quickly absorb all the fragrance, so that liquid fragrance usually remains on the surface of the ceramic body in the case of smelling immediately after vaporization or immersion. Consequently, when directly smelling the non-absorbed liquid fragrance, saturation by ethanol is very high, which makes it impossible to appreciate other notes having less fragrance so well. A further disadvantage associated with the use of ceramic bodies for testing fragrances in prior art devices is that they only allow background notes to be appreciated, and fresh notes are not appreciated if it has been a while since the initial application of fragrance on the ceramic since the perfume applied thereon dries up. Another disadvantage relating to the use of ceramic bodies is that frequent application of the fragrance is required. In addition, ceramics are susceptible to oxidation and, as with paper strips, the odour of the fragrance applied evolves over time, producing different odour profiles. In practice, although the use of ceramic bodies allows the character of the perfume to be recognized, this has lost all fidelity when delivered, or rusty notes extraneous to the original perfume appear over time. Still another disadvantage of the use of ceramic bodies is that they are prone to staining in areas where the fragrance is applied.

A device for testing fragrances and the like is described below, which allows disadvantages associated with prior art devices to be overcome and which further provides other significant advantages, as it will be seen hereafter.

SUMMARY

The present device is primarily intended to allow a user to test a fragrance, such as a perfume, for example, before being acquired. The present device, however, is of general application to any composition that can be tested, such as, for example, detergents, softeners, oils, air fresheners for clothes, air fresheners for open spaces, etc. and, in general, odour compositions.

The present device for testing fragrances and the like comprises a container which is adapted to contain therein an amount of fragrance, usually in the liquid or gel state. Other compositions are not ruled out. The container has at least one opening, for example, at the top thereof. However, the arrangement of a container with more than one opening and said opening or openings being located in other portions of the container are not ruled out.

The device for testing fragrances and the like further includes an absorbing element. Said absorbing element serves the purpose of carrying the fragrance from the inside of the container to the outside. The absorbing element of the present device can be made of, for example, a ceramic material, although it can be made of other different materials, provided that they are capable of absorbing a substance, such as a liquid substance, and that they do not have any odour so that perception of the fragrance is not altered. Examples of materials that can be used for making the absorbing element of the present device are porous materials, such as cotton, cellulose, neutral wood, pumice stone, porcelain, rigid foams, rigid rubbers, silica structures or calcium silicates (glass, aerogels), synthetic materials such as polymethylsiloxane, vermiculite, fabric, non-woven fabric, polymers, plastic fibres (PP, PET, PLA . . . ), ceramics, metal foams, plastic or metal sinters, etc. Other materials or combinations thereof are however not ruled out.

The absorbing element has a first portion and a second portion. As used herein, the terms "first portion" and "second portion" may refer to physical parts, that is, the case where the absorbing element is formed by two or more physical pieces, for example, of different materials, and also to imaginary portions, that is, the case where the absorbing element is formed by a single piece in which two or more areas are defined in said one piece.

According to an important feature of the present device, the first portion of the absorbing element is intended to be received within the container, continually in direct contact with the fragrance contained therein. The second portion of the absorbing element is intended to be at least partially outside the container, passing through said opening, which can remain in contact with the external environment. In one preferred example of the present device, the absorbing element is a rod-shaped porous material, which is partially submerged into the fragrance in the liquid state contained within the container. The absorbing element may be solid, entirely hollow, or partially hollow.

According to a further important feature of the present device for testing fragrances and the like, a cover is also provided which is intended to at least partially cover the second portion of the absorbing element. Said cover is configured, e.g. sized and/or shaped, to suitably cover the second portion of the absorbing element, that is, the one on the outside of the container. The cover of the device is configured to cover the second portion of the absorbing element in at least a substantially fluid-tight and impermeable manner.

As used herein, the term "fluid-tight" refers to the fact that the second portion of the absorbing element may be completely closed by the cover of the device without communication with the outside of the container. Also, as used herein, the term "impermeable" refers to the fact that the second portion of the absorbing element may be closed by the cover of the device in a manner that liquid of or odour is prevented from being released to the outside.

It is preferred that the cover is at least partially made of an absorbing material. As used herein, the term "absorbing" refers to a material capable of at least temporarily absorbing and retaining a fluid. As an example of an absorbing material, the cover may be made of a porous material, or it may contain therein a portion made of an absorbing material, such as a porous material, capable of being impregnated by the fragrance contained within the container, which is transmitted through the above mentioned absorbing element. As used herein, the term "porous" refers to a material having interstices, cavities or tiny holes in its composition.

In some cases, it is envisaged that the cover may have an inner cavity defining a chamber. Said chamber may be configured, e.g. sized and shaped, so that it is suitable to at least partially receive the second portion of the absorbing element, with said portion of the absorbing element being allowed or not to be in contact with the cover when the cover is closed, that is, on the container covering the absorbing element.

When the cover is closed, that is, arranged on the container covering the absorbing element, it may remain in contact with the second portion of the absorbing element, or it may be arranged in said closed position with such chamber defined between the cover and the second portion of the absorbing element. This may be suitable for compounds less rich in volatile materials or for oily materials, as the case may be. One variant is also envisaged where the cover is always in contact with the second portion of the absorbing element, which corresponds to a case where the cover is removed from the container together with the second portion of the absorbing element.

Thus, the cover, whether it is made of an absorbing material, or it includes an absorbing material contained therein, contains fragrance that has been transferred by the absorbing element from the inside of the container, as described above, so that the cover itself acts as an olfaction point, with the advantages of being shielded from the outside. The fact that, in use, the cover is impregnated with the fragrance, has the advantage of a great comfort of use, since the user smells the fragrance bringing the cover to her/his nose without having to approach the device, and without having to remove the absorbing element from the inside of the container avoiding drops or spillages. Since the fragrance is smelled directly, with the cover outside the device, there is no excess fragrance and the user does not therefore have an unpleasant and irritating sensation of smelling an alcoholic formulation as occurs in other conventional devices.

As mentioned above, the cover may be releasable from the container so as to leave the absorbing element exposed to the outside and to allow the fragrance to be released to test it, bringing it close to the nose to smell it. However, variants where the cover is attached or rotatably coupled to the container are not ruled out. Many other configurations are possible. A very easy and comfortable device is thus obtained by the ease of moving the cover to the nose avoiding having to bring the nose closer to the absorbing element. This advantage is especially important if there is more than one person testing fragrances at a time.

As stated above, the cover, when closed at least partially covering the absorbing element, is continuously impregnated with the fragrance of the container, thanks to the particular configuration described, through the absorbing element. In turn, the cover also provides an effective blockage to release of fragrance when the device is with the cover in the closed position.

The fact that it is not necessary to remove the absorbing element from the container is a great advantage for reasons of comfort and simplicity of use and because it has been found that the fact that the absorbing element is in permanent contact with the fragrance in a liquid state does not involve any dripping problems. In the above mentioned prior art known devices, the most volatile products are initially lost and, at the end, only the less volatile products remain, which involves that the user is receiving a different impression over time.

If the cover itself is formed from an absorbing material it is preferred that it includes an impermeable outer coating. Likewise, if the cover is provided with an absorbing material therein, the outer portion of the cover is made of an impermeable material. This allows the cover to be externally insulated from the inside of the container, preventing the user from getting impregnated with the fragrance when taking it.

Therefore, in the proposed device the cover is a functional element at the olfactory level, that is, the cover is the element that is smelled by the user to test the fragrance. The cover in the proposed device is therefore not limited to perform a container containment or closure function.

The present device has a very simple configuration with which many significant advantages are obtained with respect to the devices known so far. The fragrance contained in the container of the present device ascends by capillarity through the absorbing element from the first portion to the second portion thereof, unlike devices known so far where the absorbing element is already impregnated and the fragrance evaporates. In the present device, the ceramic is reloaded with fragrance on demand. The fragrance is replenished as it evaporates, so there is no overload of fragrance or lack of fragrance. Only just the amount of fragrance that is needed for the test is released and its use is limited with the cover.

A further advantage of the above described configuration is that there is less risk of fragrance loss during the use of the device since, as pointed out, the user does not have to remove the absorbing element from the container, but simply release the cover, for example, lifting it, rotating it, etc., with respect to the container, to smell the fragrance impregnated in the cover.

A suitable closure element, such as a screw cap, may be provided for closing the container. The above mentioned opening of the container may be formed in said closure element for the passage of the second portion of the absorbing element.

The cover of the device may extend up to said closure element, for example, being supported thereon. In other examples, the cover of the device may extend up to a portion of the container, entirely or partially covering it. In some cases, the cover may be adapted to be inserted into a decorative element intended to be exposed to the outside of the device. Thus, the cover might be configured, for example, as a disc, inserted into a decorative figure. Other configurations are however not ruled out.

The absorbing element and/or the closure element may have at least one fluid pathway. Said fluid pathway may be configured, for example, as one or more of a channel, a groove, a hole, a corrugation, or others, or combinations thereof, to compensate for a pressure increase within the container. Other configurations are also possible. Said fluid pathway may be formed, for example, in an inner ring that is coupled to the closure element.

It is also envisaged that the present device may further comprise a receptacle configured for receiving at least said container therein. Such receptacle is provided with an opening through which the second portion of the absorbing element that is outside the container is allowed to at least partially pass. The opening of the receptacle may be sized in such a way that the cover is allowed to at least partially pass through.

A device for testing fragrances, in particular perfumes, and similar substances with the above described configuration solves the aforementioned disadvantages and problems with reference to the devices that for the same purpose had been used so far and, at the same time, it has been found that it provides many significant advantages.

On the one hand, the present device is self-impregnated, so that it is always loaded with fragrance until it is exhausted in the container, which may happen after weeks or months depending on the container volume. It is therefore not necessary for the absorbing element to be loaded or impregnated with the fragrance very frequently. In contrast, in conventional devices, either at the time of smelling the fragrance or with a certain frequency, the absorbing element is required to be removed from the container, sprayed it with the fragrance, and then arranged it back again therein to smell the fragrance. This is a more uncomfortable operation and, in addition, the container is required to be loaded with fragrance frequently.

The fact that, in the present device, the absorbing element is impregnated on its own as the fragrance evaporates, with continued absorption, prevents the absorbing element from experiencing drying and reloading cycles, i.e. periods that are drier than others, are therefore avoided, and the exposure of the fragrance to oxidation is thus much lower, unlike in prior art devices. Furthermore, due to the above described configuration of the present device, perfume oxidation does not occur, liquid evaporation is minimized, and contact with external environment is avoided. Continued absorption of the fragrance allows for a longer duration at the point of sale by limiting the evaporation of the fragrance, unlike prior art devices, especially in fragrances with alcoholic formulations.

Furthermore, with the described device it has been found that a more constant olfactory profile is obtained throughout its useful life, keeping the odour stable. In the absence of drying of the absorbing element, the olfactory profile is always the same, unlike the devices known hitherto where fragrance odour is not the same when the absorbing element has just been impregnated as compared to some time afterwards. Thus, as stated above, in the present device no changes exist in the fragrance profile depending on when it is smelled, keeping the absorbing element odour constant, without over-representation of ethanol, when for example the fragrance is a perfume, since no fragrance remains on its surface. Therefore, there are no changes in the olfactory profile, which is faithful to the product that is being marketed, which allows working with the same formulation for both the test fragrance and the fragrance that is being marketed.

A further significant advantage of the present device is that it produces less environmental pollution, which is especially important in points of sale where there is a large number of fragrances to be tested. As a consequence of the lower environmental pollution, several devices can be arranged at a smaller distance between them, that is, different fragrances can be placed closer together.

The proposed device is based on a direct and controlled capillary transfer mechanism of the fragrance through the material of the absorbing element, which makes the user's olfactory perception similar at all times. The amount of fragrance that is impregnated in the cover is controlled by the porosity of the absorbing material selected, which results in the amount of fragrance that is actually delivered to the nose of the user always being adequate, since the absorbing element is always impregnated with the right amount of fragrance admitted by the material of the absorbing element. It is thus the absorbing element material itself that automatically regulates its impregnation according to use and its exposure to the consumer, as indicated. This is a difference with respect to the prior art devices, where the absorbing element is impregnated with the fragrance with certain periodicity and the absorbing element is then enclosed in the container to avoid part of the evaporation thereof, generating a gas phase that impregnates it. In said prior art devices, if the absorbing element is not reloaded, it dries and loses fidelity to the initial perfume. When the absorbing element dries, oxidations and odours strange to formulation occur. Also in prior art devices, once the absorbing element has been loaded with fragrance, odour qualities are lost as the device is used since the composition varies, as a result of which the quality of the fragrance becomes altered when oxidation occurs.

In the proposed system, the passage of the fragrance through the absorbing element causes odour modification over time to be much less and that the olfactory quality is therefore maintained for a longer time for the sample with respect to prior art devices where the fragrance is periodically sprayed into a ceramic body, as mentioned above.

Finally, although it has been found that the above described device for testing fragrances and the like is suitable for both ethanolic and oily formulations, being especially interesting for the former, the present device is suitable for a wide range of other many compositions giving off odour, with which a very fresh and non-aggressive odour is provided due to the appropriate amount of fragrance being impregnated in a controlled manner in the absorbing element, which is perceived by the user without excesses that might be annoying for olfaction.

Additional objects, advantages and features of examples of the device for testing fragrances and the like will become apparent to those skilled in the art upon examination of the description, or may be learned by practice thereof.

BRIEF DESCRIPTION OF THE DRAWINGS

Particular examples of the present device for testing fragrances and the like will be described in the following, by way of non-limiting examples, with reference to the figures of the appended drawings, in which.

DETAILED DESCRIPTION OF EXAMPLES

Figure 1:
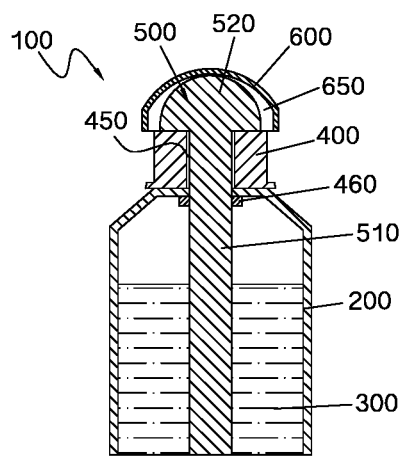
FIG. 1 is a sectional view of a first example of the device for testing fragrances and the like, with the cover configured extending to the top of the closure element, and wherein the absorbing element is formed by a single piece.
Figure 2:
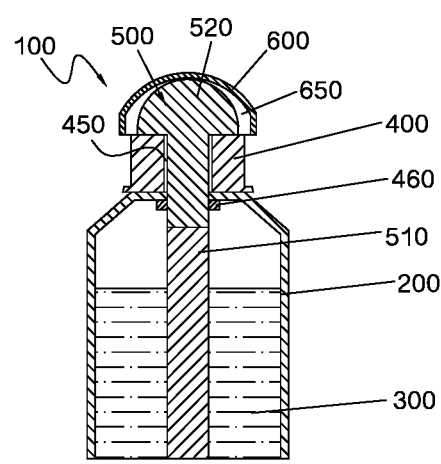
FIG. 2 is a sectional view of a second example of the device for testing fragrances and the like, with the cover configured extending to the top of the closure element, and wherein the absorbing element is formed by two pieces.
Figure 3:
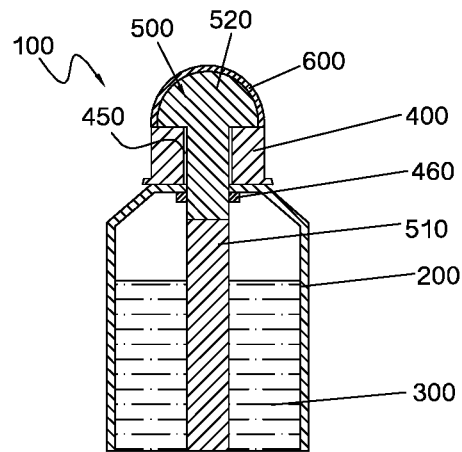
FIG. 3 is a sectional view of a third example of the device for testing fragrances and the like, with the cover configured extending to the top of the container, and wherein the absorbing element is formed by two pieces.

Several non-limiting examples of the present device for testing fragrances and the like have been illustrated in FIGS. 1-9 of the drawings. The device has been designated as a whole by reference numeral 100.

In all the examples illustrated and described herein, the device 100 is used to test a perfume 300. The device 100 can be however used to test any type of fragrance, in addition to perfume, such as, for example, detergent, softener, oil, air freshener, etc. and, in general, any odour compositions that can be tested before being acquired.

In all the examples illustrated in FIGS. 1-9 of the drawings, the device 100 comprises a container 200 made of plastic, glass, or any other suitable material. The container 200 has, in the illustrated examples, a generally cylindrical overall configuration, although other configurations, such as prismatic, spherical, oval, combinations thereof, or even irregular, are not ruled out. The container 200 may be either transparent in order to see the amount of perfume 300 contained therein, opaque, or translucent, having decorations, colours, etc.

Figure 9:
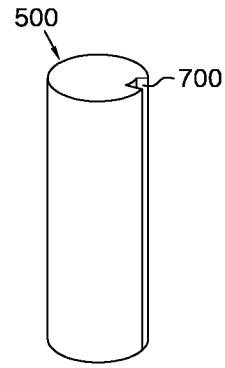
FIG. 9 is a perspective view of one example of an absorbing element.

The device 100 illustrated in all the examples shown includes, in addition, an absorbing element 500. The absorbing element 500 shown in the non-limiting example of FIG. 9 is rod-shaped although many other configurations are not ruled out. The absorbing element 500 is made of a high capillarity absorbing material, for example, a porous type material, capable of transporting the perfume 300 from the inside of the container 200 to the outside.

Figure 4:
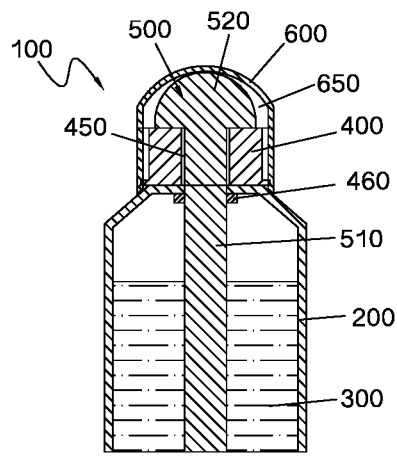
FIG. 4 is a sectional view of a fourth example of the device for testing fragrances and the like, with the cover configured extending to the top of the container, and wherein the absorbing element is formed by one piece.
Figure 5:
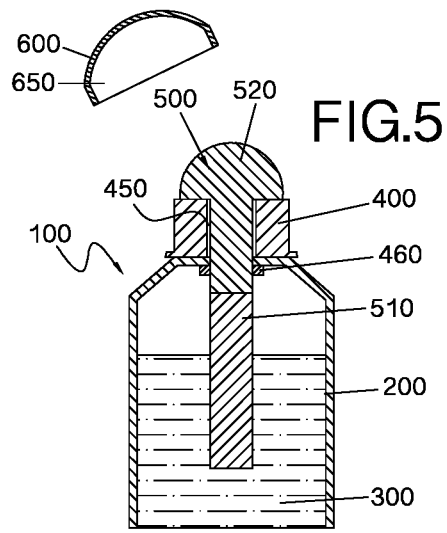
FIG. 5 is a sectional view of a fifth example of the device for testing fragrances and the like, similar to the second example in FIG. 2, with the cover removed from the device.
Figure 6:
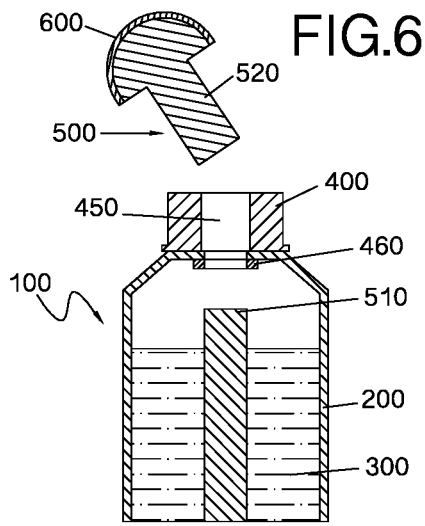
FIG. 6 is a sectional view of a sixth example of the device for testing fragrances and the like, similar to the second and fifth examples in FIGS. 2 and 5, respectively, and with the cover removed from the device, together with one portion of the absorbing element.
Figure 7:
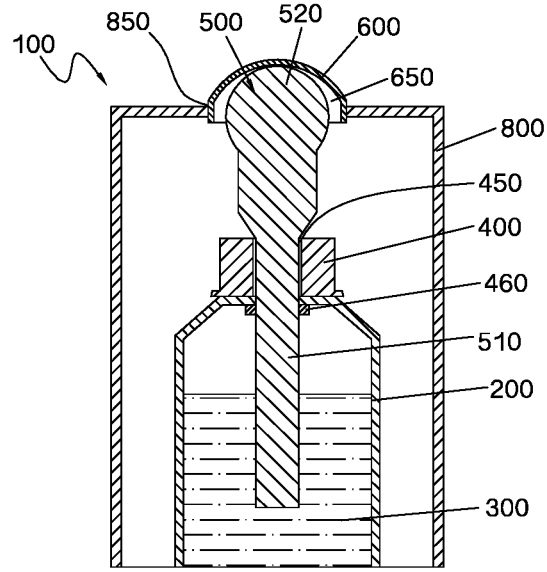
FIG. 7 is a sectional view of a seventh example of the device for testing fragrances and the like, including a receptacle.

In the examples illustrated in FIGS. 1, 4 and 7, the absorbing element 500 is formed by a single piece while, in the examples illustrated in FIGS. 2, 3 and 5, 6, the absorbing element 500 is formed by two pieces. In any case, in all the examples, two portions 510, 520 are defined in the absorbing element 500 which may be independent pieces (FIGS. 2, 3, 5, 6) or simply areas of the same physical piece (FIGS. 1, 4, 7).

More specifically, in all the examples illustrated in the drawings, a first portion 510 is identified in the absorber element 500, which is intended to be received within the container 200, continuously in direct contact with the perfume 300 that is contained therein. The arrangement of the first portion 510 of the absorbing element 500 in permanent contact with the perfume 300 in the liquid state within the container 200 results in that the absorbing element 500 is continuously impregnated always by itself as the perfume 300 evaporates. Consequently, it is not necessary for the absorbing element 500 to be periodically impregnated with perfume 300, replenishing perfume 300 in the container 200 being only necessary when it is exhausted, which may happen after weeks or months depending on the volume contained in the container 200. Thanks to this configuration, oxidation of perfume 300 does not occur and evaporation is minimized, avoiding contact with external environment.

A second portion 520 is also identified in the absorbing element 500, which is partially arranged outside the container 200, through an opening 450 that is formed in a top portion of the container 200, in particular, formed in a closure element 400, which will be described later. It is clear that, in a normal use of the device, the second portion 520 of the absorbing element 500 is not in direct contact with the perfume 300 within the container 200.

The first portion 510 of the absorbing element 500 may be longer than the second portion 520 of the absorbing element 500, as shown in the figures. It is not however excluded the case where the first portion 510 of the absorbing element 500 is shorter than the second portion 520 of the absorbing element 500, or that where both parts 510, 520 have the same length. The length of the first portion 510 of the absorbing element 500 may be set, for example, as a function of the maximum level of perfume 300 within the container 200. The first portion 510 of the absorbing element 500 may extend up to the maximum level of perfume 300 within the container 200 or even further, until reaching the neck of the container 200, in some cases.

The device 100 also includes, in all the examples, a cover 600. The cover 600 is configured to cover, in a fluid-tight and impermeable manner, the second portion 520 of the absorbing element 500, that is, the portion of the absorbing element 500 arranged outside. The cover 600 is made of an absorbing material, or it contains an absorbing material therein, such as, for example, a porous material, impregnable by the perfume 300 that is transmitted by capillarity from the inside of the container 200. If the cover 600 is made of an absorbing material, it may include a liquid-tight coating to provide insulation from the inside of the container 200. This prevents the user from being impregnated with perfume 300 when taking the cover 600, for example, for releasing it from the device, or for coupling it thereto. The cover 600 might however not be made of an absorbing material, but contain a part with an absorbing material therein. In any case, the cover 600, whether it is entirely made of an absorbing material or it contains an absorbing material therein, is adapted to collect the perfume 300 that is transported by the absorbing element 500 from the inside of the container 200. In this way, removing the absorbing element 500 from the container 200 to smell the perfume 300 is not necessary but it is sufficient to take the cover 600 to the nose, once it has been released from the container 200, and smell it.

In the example illustrated in FIGS. 1, 2, 4, 5 and 7, the cover 600 has an inner cavity 650 defining a chamber or space suitable for receiving the second portion 520 of the absorbing element 500, which is outside the container 200. In the example illustrated in FIGS. 3 and 6, however, the inner cavity 650 is suitable for receiving the second portion 520 of the absorbing element 500 so that both are in contact. In any case, the perfume 300 is transmitted from the absorbing element 500 to the inside of the cover 600, impregnating it continuously, as indicated above. The cover 600 thus acts as an olfaction point, so that the user simply has to remove it, for example, by separating, lifting, moving away, turning, etc. the cover 600 from the container 200 so that the absorbing element 500 is exposed, and to smell it near the nose. The user can thus directly smell the perfume 300 in a comfortable and simple way, without excess perfume 300 being produced and thus avoiding unpleasant and irritating sensations.

Figure 8:
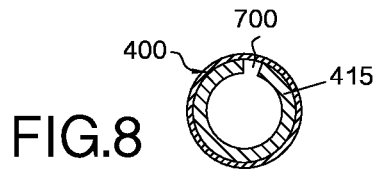
FIG. 8 is a sectional view of one example of a closure element.

In the examples shown in FIGS. 1-7, a closure element 400 is provided, as indicated above. A sectional view of the closure element 400 is shown in FIG. 8. The closure element is configured as a screw cap 400 with an opening 450 for the passage of the absorbing element 500 therethrough. The cap 400 is intended to be screwed to the neck of the container 200 so as to close it properly.

In the example illustrated in FIGS. 1-3, and 5-6 the cover 600 extends to the top of the closure element 400. By contrast, in the example illustrated in FIG. 4, the cover 600 extends into a portion of the container 200. However, cases are envisaged where the cover 600 extends entirely or partially covering the container 200 and even cases, such as the example illustrated in FIG. 7, where the cover 600 extends into a receptacle 800 that externally covers the entire container 200. Said receptacle 800 will be described further below. Also, the cover 600 may be adapted to be inserted into a decorative element, not shown.

FIGS. 8 and 9 of the drawings show examples of a fluid pathway 700 formed in the closure element 400 and in the absorbing element 500, respectively. The fluid pathway 700 is intended to compensate for a pressure increase within the container 200. In particular, in the case of FIG. 8, the fluid pathway 700 is formed in the closure element 400 and, more specifically, in an inner ring 410 coupled or inserted into the closure element 400 while, in the case of FIG. 9, the fluid pathway 700 is formed in the absorbing element 500. Other options are possible, such as, for example, arranging a fluid pathway 700 formed internally in the same material of the closure element 400, or formed both in the closure element 400 and in the absorbing element 500. In the particular example illustrated in FIGS. 8 and 9, the fluid pathway 700 is configured as a small sized U-shaped channel to avoid evaporation and contamination. The channel 700 is formed radially in the closure element 400, or longitudinally in the absorbing element 500. However, other configurations for the fluid pathway 700, such as in the form of a groove, hole, or corrugation, are not ruled out, having a continuous or irregular shape, with various sizes and shapes, as appropriate.

In the non-limiting example illustrated in FIG. 7, the device 100 further comprises a receptacle 800, as indicated above. The receptacle 800 is configured to externally cover the entire container 200, and also partially the absorbing element 500. The receptacle 800 may be formed of metal, plastic, or other suitable material, and may be opaque, translucent, or transparent, and may even include decorative elements. In the non-limiting example illustrated in said FIG. 7, the receptacle 800 has a cylindrical configuration with no lower base and with an opening 850 at the top through which the second portion 520 of the absorbing element 500 is allowed to partially pass. The cover 600 may be received in the opening 850 of the receptacle 800, as shown in said FIG. 7.

Although only a number of particular examples of the present device for testing fragrances and the like have been described herein, it will be understood by those skilled in the art that other alternative examples and/or uses and obvious modifications and equivalents thereof are possible.

Thus, there exist many compositions that can be used with the present device, in addition to fragrances, and in various states, in addition to the liquid state. On the other hand, the container of the device may have different shapes apart from the generally cylindrical shape described above, with one or several openings formed in different areas thereof. Also, the absorbing element may be formed of an absorbing material or a combination of suitable absorbing materials capable of being impregnated with an odour composition. Likewise, the absorbing element may be formed by a single piece with one or several areas defined therein, equal or different in length, or it may be formed by several pieces, equal or different in length. A number of configurations and shapes for the cover are also envisaged, for example, disc-shaped, oval-shaped, etc., and also different means for coupling to the device in general, or to the container, such as press fitted, pivotally coupled, etc. Finally, the fluid pathway to compensate for pressure increases within the container may have multiple configurations, in addition to the above described shape of groove, hole, or corrugation, with straight, curved, and/or with continuous or discontinuous configurations, etc. being possible.

The present disclosure therefore covers all possible combinations of the particular examples described herein. Thus, the scope of the present description should not be limited by particular examples described herein, but should be determined only by a fair reading of the claims that follow. Reference signs related to drawings and placed in parentheses in a claim, are solely for attempting to increase the intelligibility of the claim, and shall not be construed as limiting the scope of the claim.

The invention claimed is:

1. A device for testing fragrances, comprising:
   a container adapted to contain a fragrance which has at least one opening;
   a removable cover comprising a fluid-tight and impermeable coating and an inner absorbing or porous material, wherein the fluid-tight and impermeable coating and the inner absorbing or porous material is attachable to and detachable from the container upon attaching the cover to and detaching the cover from the container; and
   an absorbing element having
   (i) a first portion configured to be housed within the container and continuously in direct contact with the fragrance, and
   (ii) a second portion configured to move away from the first portion upon removal of the cover from the container, and configured to be displaced out of the opening and to an outside the container when the cover is removed from the container, and the second portion projecting outwardly from the cover towards the first portion through the opening when the cover is attached to the container;
   wherein the cover is configured to at least partially cover the second portion of the absorbing element, the cover comprising the fluid-tight and impermeable coating to insulate the fragrance inside of the container and the inner absorbing or porous material to allow the fragrance to be transmitted to the inner absorbing or porous material from the absorbing element such that an inner cavity of the cover acts as an olfaction point allowing a user to smell the fragrance from the inner cavity only after releasing the cover from the container.

2. The device of claim 1, wherein the cover is releasable from the absorbing element to leave the absorbing element exposed and to allow the fragrance to be released so as to test the fragrance.

3. The device of claim 1, wherein the cover has the inner cavity defining a chamber suitable to at least partially receive the second portion of the absorbing element.

4. The device of claim 3, wherein the inner cavity is sized such that the second portion of the absorbing element is in contact therewith when the cover is arranged covering the absorbing element.

5. The device of claim 1, additionally comprising a closure element configured to close the container, said opening being formed in the closure element.

6. The device of claim 5, wherein the closure element has at least one fluid pathway intended to compensate for a pressure increase within the container.

7. The device of claim 5, wherein the cover extends into the closure element.

8. The device of claim 1, wherein the absorbing element is made of a ceramic material.

9. The device of claim 1, wherein the absorbing element has at least one fluid pathway intended to compensate for a pressure increase within the container.

10. The device of claim 9, wherein said fluid pathway is formed by one or more of a channel, a groove, a hole, or a corrugation.

11. The device of claim 1, wherein the absorbing element is formed of different materials.

12. The device of claim 1, wherein the cover extends into a portion of the container.

13. The device of claim 1, wherein the cover extends covering the container.

14. The device of claim 1, wherein the cover is adapted to be inserted into a decorative element intended to be exposed to the outside of the device.

15. The device of claim 1, further comprising a receptacle configured for receiving at least the container, the receptacle having an opening through which the second portion of the absorbing element is allowed to at least partially pass to the outside of the container.

16. The device of claim 15, wherein the opening of the receptacle is sized such that the cover is allowed to at least partially pass through.

* * * * *